United States Patent
Anavi et al.

(10) Patent No.: US 10,111,632 B2
(45) Date of Patent: Oct. 30, 2018

(54) SYSTEM AND METHOD FOR BREAST CANCER DETECTION IN X-RAY IMAGES

(71) Applicant: Siemens Healthcare GmbH, Erlangen (DE)

(72) Inventors: Yaron Anavi, Kefar Yona (IL); Atilla Peter Kiraly, Plainsboro, NJ (US); David Liu, Franklin Park, NJ (US); Shaohua Kevin Zhou, Plainsboro, NJ (US); Zhoubing Xu, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 47 days.

(21) Appl. No.: 15/420,274

(22) Filed: Jan. 31, 2017

(65) Prior Publication Data
US 2018/0214105 A1  Aug. 2, 2018

(51) Int. Cl.
| | |
|---|---|
| G06K 9/00 | (2006.01) |
| A61B 6/00 | (2006.01) |
| G06T 7/00 | (2017.01) |
| G06K 9/62 | (2006.01) |
| G06T 7/10 | (2017.01) |
| G06N 7/00 | (2006.01) |

(Continued)

(52) U.S. Cl.
CPC ............ *A61B 6/502* (2013.01); *A61B 6/5217* (2013.01); *G06K 9/6256* (2013.01); *G06K 9/6269* (2013.01); *G06N 7/005* (2013.01); *G06N 99/005* (2013.01); *G06T 7/0014* (2013.01); *G06T 7/10* (2017.01); *G06K 2209/05* (2013.01); *G06T 2207/10016* (2013.01); *G06T 2207/10116* (2013.01); *G06T 2207/20021* (2013.01); *G06T 2207/20076* (2013.01); *G06T 2207/20081* (2013.01); *G06T 2207/30068* (2013.01); *G06T 2207/30096* (2013.01)

(58) Field of Classification Search
USPC ....... 382/100, 103, 106, 128–133, 154, 155, 382/162, 168, 173, 181, 214, 224, 232, 382/254, 274, 276, 286, 291, 305, 159; 378/21, 37; 600/408
See application file for complete search history.

(56) References Cited

U.S. PATENT DOCUMENTS

| | | | | |
|---|---|---|---|---|
| 2007/0280530 A1* | 12/2007 | Fung | ................... | G06K 9/6269 382/159 |
| 2014/0153819 A1* | 6/2014 | Lin | ........................ | G06T 5/002 382/159 |

(Continued)

OTHER PUBLICATIONS

Chatfield, Ken, et al. "Return of the devil in the details: Delving deep into convolutional nets." arXiv preprint arXiv:1405.3531 (2014).

(Continued)

*Primary Examiner* — Seyed Azarian (57) ABSTRACT

For breast cancer detection with an x-ray scanner, a cascade of multiple classifiers is trained or used. One or more of the classifiers uses a deep-learnt network trained on non-x-ray data, at least initially, to extract features. Alternatively or additionally, one or more of the classifiers is trained using classification of patches rather than pixels and/or classification with regression to create additional cancer-positive partial samples.

18 Claims, 4 Drawing Sheets

CLASSIFIER 1: INTENSITIES MEAN

DEGENERATED CLASSIFIER:
IF PATCH'S MEAN PIXELS INTENSITIES IS LARGER THEN A PRE-DEFINED THRESHOLD IT IS EXAMINED BY THE FOLLOWING CLASSIFIER

CLASSIFIER 2: PROBABILITY THRESHOLD

REGRESSION MODEL:
IF PATCH PROBABILITY IS LARGER THEN A PRE-DEFINED THRESHOLD (TUNED) IT IS EXAMINED BY THE FOLLOWING CLASSIFIER USING A FEATURE VECTOR EXTRACTED FROM THE VGG NETWORK (51) Int. Cl.
  *G06N 99/00*   (2010.01)
  *A61B 6/04*    (2006.01)

(56) References Cited

U.S. PATENT DOCUMENTS

| | | | | |
|---|---|---|---|---|
| 2015/0087957 A1* | 3/2015 | Liu | ............... | G06T 7/42 |
| | | | | 600/408 |
| 2015/0196265 A1* | 7/2015 | Suzuki | ............ | G06K 9/6262 |
| | | | | 378/37 |
| 2016/0314579 A1* | 10/2016 | Ghouti | ............ | G06T 7/0012 |

OTHER PUBLICATIONS

Kainz, Philipp, et al. "You Should Use Regression to Detect Cells." International Conference on Medical Image Computing and Computer-Assisted Intervention. Springer International Publishing, 2015.

Matsubara, T., et al. "An automated method for detecting architectural distortions on mammograms using direction analysis of linear structures." 2015 37th Annual International Conference of the IEEE Engineering in Medicine and Biology Society (EMBC). IEEE, 2015.

Rangayyan, Rangaraj M., et al. "Measures of divergence of oriented patterns for the detection of architectural distortion in prior mammograms." International journal of computer assisted radiology and surgery 8.4 (2013): Abstract.

Rangayyan, Rangaraj M., Shantanu Banik, and JE Leo Desautels. "Detection of architectural distortion in prior mammograms using measures of angular dispersion." Medical Measurements and Applications Proceedings (MeMeA), 2012 IEEE International Symposium on. IEEE, 2012.

* cited by examiner

CLASSIFIER 1: INTENSITIES MEAN

DEGENERATED CLASSIFIER:
IF PATCH'S MEAN PIXELS INTENSITIES IS LARGER THEN A PRE-DEFINED THRESHOLD IT IS EXAMINED BY THE FOLLOWING CLASSIFIER

CLASSIFIER 2: PROBABILITY THRESHOLD

REGRESSION MODEL:
IF PATCH PROBABILITY IS LARGER THEN A PRE-DEFINED THRESHOLD (TUNED) IT IS EXAMINED BY THE FOLLOWING CLASSIFIER USING A FEATURE VECTOR EXTRACTED FROM THE VGG NETWORK

FIG. 6

80 — X-RAY SYSTEM
82 — PROCESSOR
84 — MEMORY
85 — USER INPUT
86 — DISPLAY

FIG. 7

SYSTEM AND METHOD FOR BREAST CANCER DETECTION IN X-RAY IMAGES

BACKGROUND

The present embodiments relate to breast cancer detection. A physician is aided in diagnosis by computer assisted detection from x-ray imaging.

Invasive breast cancer develops in about 1 of 8 U.S. women. In 2016, about 246,660 new cases of invasive breast cancer are expected to be diagnosed. Early detection of breast cancer offers the advantages of earlier treatment and better outcomes. X-ray mammography is the common screening approach used in clinics. Screening requires the precious time of the radiologist. For a growing workload, greater efficiency is demanded from radiologists' examination of mammograms.

Computerized systems may help in prioritization and diagnosis of findings. Several automated methods have been developed to increase the detection rate of breast cancer. The computerized detection systems use hand-crafted features or other feature vectors, such as GLCM, mean curvature, and edge features. The feature vectors or other image processing is used to detect breast cancer. These computerized systems may be impractical due to high false-positive rates.

SUMMARY

By way of introduction, the preferred embodiments described below include methods, systems, instructions, and non-transitory computer readable media for breast cancer detection with an x-ray scanner. A cascade of multiple classifiers is trained or used. One or more of the classifiers uses a deep-learnt network trained on non-x-ray data, at least initially, to extract features. Alternatively or additionally, one or more of the classifiers is trained using classification of patches rather than pixels and/or classification with regression to create additional cancer-positive samples.

In a first aspect, a method is provided for breast cancer detection with an x-ray scanner. A patient is scanned with the x-ray scanner. The scanning provides a frame of data representing breast tissue in the patient. Patches of the frame of data are classified as of interest or not based on intensity. A probability of breast cancer is determined for the patches that are of interest using a deep learnt regression at least partially trained on non-x-ray data. The patches with the probability over the threshold are classified using a machine-learnt classifier. An indication is displayed of breast cancer for the patient based on an output of the classifying using the machine-learnt classifier.

In a second aspect, a method is provided for machine training a classifier for breast cancer detection. A set of x-ray images with ground truth labels for first locations of breast cancer are acquired. Adjacent locations to the first locations are assigned regressed labels of breast cancer, and second locations spaced from the first locations are assigned as ground truth labels of no breast cancer. A cascade of classifiers is machine trained. At least one of the cascade of classifiers is trained using the ground truth labels of breast cancer for the first locations, the regressed labels for the adjacent locations, and the ground truth labels of no breast cancer for the second locations.

In a third aspect, a method is provided for breast cancer detection with an x-ray scanner. A patient is scanned with the x-ray scanner. The scanning provides a frame of data representing breast tissue in the patient. A probability of breast cancer for the patient is determined with a deep learnt classifier trained on image data for objects other than breast tissue. An indication of breast cancer for the patient is displayed based on the probability.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Computer assisted diagnosis helps breast cancer detection in x-ray images. Traditional methods tend to produce higher levels of false positives (i.e., unnecessarily marked location) and false negatives (i.e., missed detections), resulting in additional reading time by a radiologist. To reduce false positives and false negatives and to better assist the radiologist, multiple phases of evaluation are implemented by the computer assisted diagnosis. The cascade of classifiers allows implementation of simple classifiers for larger data and more complex classifiers for reduced data, so may provide assistance that is fast and accurate to avoid costing more time.

In one embodiment, the cascade uses regression and deep learning regression for breast cancer cases. The initial cascades are comprised of simple binary classifiers while the final classifier results in a regression output for the cancer region. By using regression, the cascade may be trained and operate with a smaller annotated database of breast cancer images. By using distance-based regression and patch classification, additional partial-positive regions of the image may be introduced into the training set. Further classification on the output regression map may reveal the exact location present in the original labels. The application of a more complex classifier is performed in a sparse fashion by reducing the regions to be examined using classification early in the cascade.

Deep learning provides the best predictive power when the dataset is large enough. Such data is often expensive or tedious to individually label or difficult to obtain in large quantities. A lack of annotated breast cancer data makes the training process to build a proper model without overfitting the training data difficult. The regression may counter the lack of annotated breast cancer cases. By applying a deep-learnt network in the classification, the detection may be more efficient. The regression augments the available dataset by extending the less frequent (e.g., cancer positive) class according to certainty, allowing use of predictive power provided by deep learning. Using a deep-learnt network trained on other types of imaging may also counter a lack of annotated breast cancer data. Using deep-learnt networks based on non-x-ray or medical data allows use of the deep-learnt network with potential less x-ray examples in the training set.

The cascade of classifiers may be used for imaging other than x-ray imaging and/or for detection of abnormalities other than breast cancer. The cascade is a general and adaptive deep learning methodology to detect abnormalities in 2D, 3D, or 4D medical images.

Figure 1:
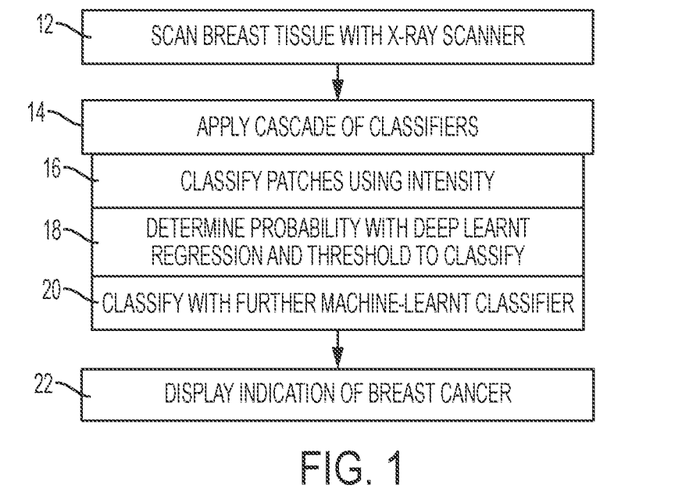
FIG. 1 is a flow chart diagram of one embodiment of a method for breast cancer detection with an x-ray scanner.

FIG. 1 is a flow chart of one embodiment of a method for breast cancer detection with an x-ray scanner. A cascade classification system includes n classifiers where n>1. The cascade optimizes classification time and accuracy by having a simple classifier eliminating easy cases as the first, early, or prior step. The second or following classifier may be of more complexity operating on smaller but possible more difficult to classify sections. The flow chart of FIG. 1 uses n=3 (see acts 16-20), but other values of n or numbers of classifiers may be used in the cascade (see FIG. 6).

Figure 7:
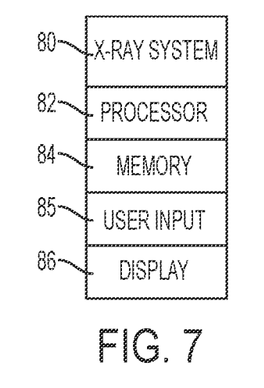
FIG. 7 is one embodiment of a system for breast cancer detection.

The method is performed with the system of FIG. 7 or a different system. For example, an x-ray imager or scanner performs act 12. A computer, server, or other processor performs acts 14-20. The processor may be part of or separate from the x-ray scanner. A display of the x-ray scanner or a separate display is used to perform act 22.

The acts are performed in the order shown (e.g., top to bottom) or other orders. Additional, different, or fewer acts may be provided. For example, additional classifiers are provided in the cascade of act 14, occurring before or after any of acts 16-20. As another example, only two of three of the classifications of acts 16-20 are performed. Acts 18 and 20 may be combined into one act.

In act 12, an x-ray scanner scans breast tissue. One or more x-ray images or datasets are acquired. Each x-ray image is a frame of data representing a breast of the patient. The data may be in any format. While the terms "image" and "imaging" are used, the image or imaging data may be in a format prior to actual display of the image. For example, the x-ray image may be a plurality of scalar values representing different locations in a Cartesian or detector format. As another example, the x-ray image may be a plurality red, green, blue (e.g., RGB) values output to a display for generating the image in the display format. The x-ray image may not yet be a displayed image, may be a currently displayed image, or may be previously displayed image in the display or another format. The image or imaging is a dataset that may be used for imaging, such as scan data representing the patient.

The x-ray image or frame of data is from mammography or is a mammogram. An x-ray source and detector are positioned relative to a breast and at a desired imaging direction. The detector detects the attenuation of the x-rays passing through the breast. The resulting frame of data may be processed or segmented to remove non-breast tissue or to isolate breast tissue. Any standard or non-standard mammography image may be used. One frame of data is acquired, but multiple frames of data may be acquired, such as frames of data from x-ray scanning along orthogonal directions relative to a breast. Other types of x-ray images may be used.

The frame of data represents a three-dimensional region of the patient projected to a plane of the detector. The frame of data represents an x-ray projection through the breast tissue, so each pixel or measure is of the accumulated attenuation of x-rays from the source to the detector. Values are provided for each of multiple locations distributed in two dimensions. A tumor or suspicious tissue (e.g., cancer) within the patient may be represented by the values of the frame of data.

In other embodiments, other tissue than breast tissue is scanned. The cascade is applied to cancer, tumor, or other abnormality detection for other tissues.

In act 14, a processor applies a cascade of classifiers. The cascade includes two or more classifiers. In the example of FIG. 1, three classifiers are used (i.e., acts 16-20). Each classifier is designed to use the output of one or more of the previous classifiers. For example, a first classifier is used to reduce the number of locations to be classified by a second classifier. This reduction in locations allows for more complex and/or rapid classification than if the second classifier were applied to all the breast tissue locations represented by the frame of data. Each classifier indicates a likelihood of breast cancer, either as a binary or as a non-binary (e.g., probability) output.

Acts 16, 18, and 20 show three classifiers in the cascade. Different classifiers may be used for any phase or classifier of the cascade. Each classifier is of a different or same type (e.g., support vector machine-learnt classifier) as other classifiers in the cascade. Each classifier is designed to operate on the available inputs at that stage or phase of the cascade. Using the same type of classifier in different phases may result in different classifiers based on the stage or phase, available information at that phase, and/or any difference in input feature vector.

In act 16, patches are classified in a first phase of the cascade. The frame of data is divided into non-overlapping patches, such as square regions. Each patch is a distinct area from the other patches. Overlapping patches may be used with any amount of overlap. Any number and/or size of patches may be used. For example, the first phase involves a scan of the image by examining a relatively small number (e.g., 100) of square patches. The patches are for the entire frame or just segmented breast tissue regions.

The patches are classified so that patches with no cancer indication are not further processed in other phases of the cascade. Only the patches classified as possibly showing cancer by this first phase are passed on to subsequent classifiers.

The classification or classifier is of any type. For example, a machine-trained classifier is used. As another example, a filter or image process and threshold is used. In yet another example, template matching or correlation is used. Combinations of approaches may be used, such as applying image processing and using machine learning to determine a threshold and/or to distinguish a patch representing cancer from a patch not representing cancer.

In one embodiment, the classifier averages the intensity or scalar values of the x-ray frame of data for the patch. Other statistical measures of the intensity may be used. This mean intensity for each patch is compared to a threshold. The threshold distinguishes between cancer and no cancer. Patches that have a higher mean intensity may more likely represent cancer within the patch. The mean intensity is used to classify each patch. Patches that are identified as ones with relatively high mean intensity value are examined by a second classifier in the second phase.

Figure 2:
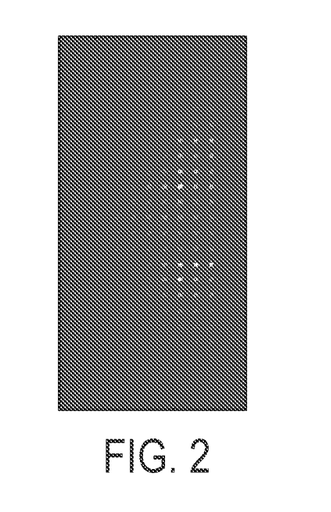
FIG. 2 represents an example sparse classification based on intensity.

FIG. 2 shows an example of the first phase of classification. The dots represent mean intensity at the center of respective patches over breast tissue. The left, upper, and lower regions are regions without breast tissue. This spatial distribution of mean intensity is a probability map obtained based on the division into patches and mean intensity by patch. The threshold completes the initial classification. The threshold may be absolute, such as only patches above a set or predetermined threshold are identified as possibly cancer. Alternatively, the threshold may be adaptive, such as identifying a given number of patches by selecting the patches with the highest means.

In act 18, another classifier is applied to the patches identified as possibly representing cancer in the previous classifier. In the second phase, patches that passed the first degenerated classifier (i.e., first phase classifier of act 16) are classified. These patches are ones with relatively high probability to contain cancer, so are classified without classifying the patches with a relatively low probability to contain cancer. Alternatively, the patches not included are almost 100% certain to not have cancer. The patches passing the first classifier are those that have any possibility of cancer.

In one embodiment, the probability of breast cancer for the patch is estimated. Rather than a binary decision, a probability with any resolution (e.g., 0-100% by 1% or 5% steps) is determined by classification. The probability may be binary in other embodiments.

Any classifier or type of classifier may be used, such as any of the classifiers discussed above for act 16. In one embodiment, the classifier is a machine-learnt classifier. Any machine learning may be used, such as a combination of a deep-learnt classifier initially trained on non-x-ray data and a regression model.

Machine learning uses a data set with known labels. For example, hundreds or thousands of x-ray images of breasts are obtained. The images are obtained from a database, scanning patients, and/or another source. Some of the images include representation of cancer. The images are labeled with the ground truth. For example, each location representing cancer is labeled as cancer and all other locations are labeled as not cancer.

To train and to use the resulting classifier, features are extracted from the frames of data. Any features may be used, such as Haar wavelets, GLCM, mean curvature, or edge features. The features may be set by a programmer. The machine learning may determine which of the programmer set features are determinative.

In one embodiment, machine learning is used to detect or create the features. Rather than relying on a programmer selecting or identifying features, a deep-learnt network is trained to create features. The deep learnt network is then used to extract feature values. Any deep learning, such as a neural network with any number or type of layers and/or nodes may be used.

Figure 3:
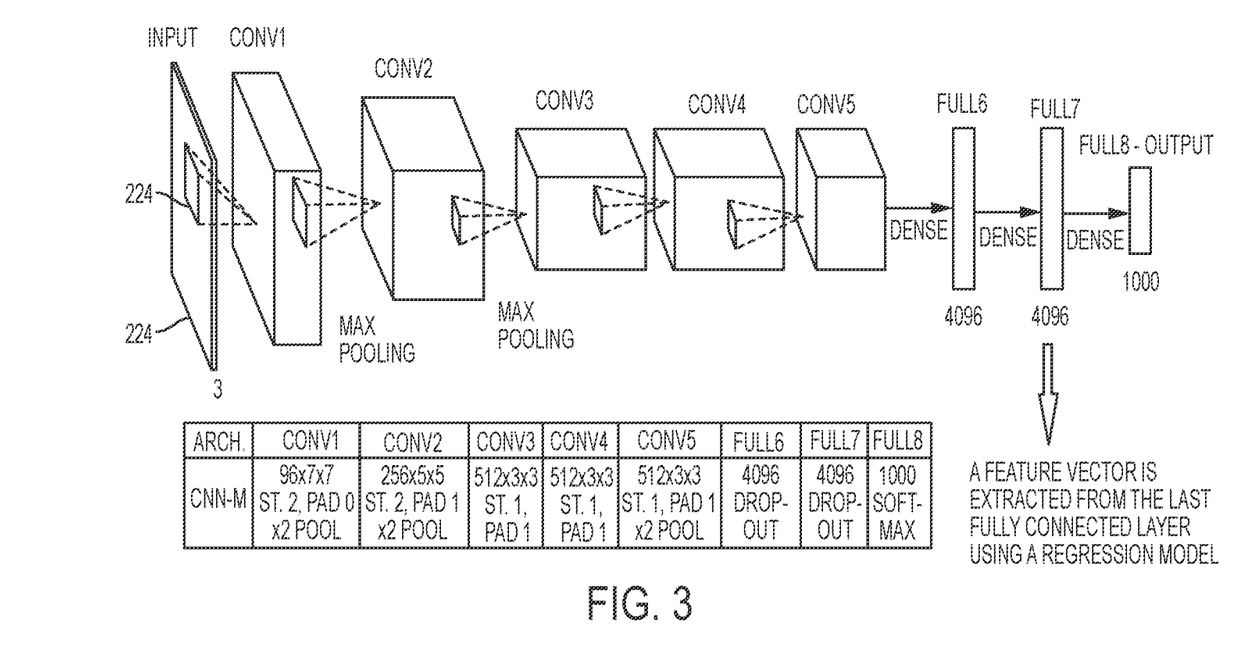
FIG. 3 represents an example deep-learnt classifier.

To deal with a limited amount of training data, a deep-learnt network is trained on image data other than x-ray data or other than medical imaging data. For example, images from optical cameras capture animals or nature scenes. Tens of thousands or more images may be used to train the deep-learnt network. Deep learning is used to learn features that distinguish between objects represented in the images. One example is a pre-trained vgg-m-4096-network represented in FIG. 3. The architecture of vgg-m-4096 (VGG) is a convolutional neural network trained on a vast amount of non-medical image data with 4096 neurons, i.e. features, in the last fully connected layer before an output layer. The VGG is trained with 224×224 images with 3 colors (e.g., RGB). For gray scale, the three colors have a same value for each channel. The table shows stride, padding, and pooling parameters in each layer. The output layer is a classifier trained to classify the object. The output of the neurons in the second to last layer are feature values. These feature values may be output without using the classifier for the non-medical imaging. A patch of any size is fed into the network, and a feature vector of the size 4096 is extracted from the last fully connected layer of the VGG. A feedforward operation is used to obtain the 4096 feature values. These feature values may be used to extract feature values for patches of x-ray frames of data.

The deep learnt network is used without modification. To train a model and build a classifier, cancer and non-cancer patches are translated to feature vectors using the pre-trained deep-learnt network without any training with x-ray images. Alternatively, the deep-learnt network is used as a starting point. Patches from training data of x-ray images of the breast are used to modify the deep learnt network, tuning the pre-trained deep learnt network. The tuning is performed as part of machine training a classifier to output the probability based on the values of the input feature vector from the deep-learnt network.

For application of the classifier for a given patient, values for any number of features are extracted from the patches of interest. The values for a texture of the tissue represented by the patch are extracted. The texture of the tissue is represented by the measures of the patch. The extraction of the values for each feature is performed for the tissue region of interest, avoiding application to other tissue outside the region of interest. Alternatively, the values for other regions outside the region of interest are extracted.

Each feature defines a kernel for convolution with the data. The results of the convolution are a value of the feature. By placing the kernel at different locations, values for that feature at different locations are provided. Given one feature, the values of that feature at different locations in the patch are calculated. Multiple feature values are calculated for each patch. Features for other texture information than convolution may be used, such as identifying a maximum or minimum. Other features than texture information may be used.

Where a cascade is used, the classifiers may be trained in the cascade. The previous classifier reduces the set of data to more difficult cases for a more advanced and more focused later stage classifier. Rather than passing features or other output, the preceding classifier identifies patches of interest for further classification. The patch is passed.

Providing more breast cancer examples in the training set results in a better machine-learnt classifier. The training data is used to associate combinations of image features with the ground truth label, resulting in a matrix of relationship between feature values and the ground truth label. By having more training data, the relationship or statistical relations may be more accurate.

It may be costly or difficult to acquire training data. To overcome sparsity of training examples, a regression model may be used. The regression model is used in one or more of the classifiers. The classification is formulated as a regression problem. Training samples of non-cancer regions that contain cancerous regions on the borders may create confusion since cancerous regions are still processed and evaluated into a non-cancerous region. In the regression model in the cascade, a region is detected instead of a single point since the cancer label is for a region.

To allow for more positive and variable types of regions to be included in the detection phase, the positive training dataset is extended by regression. Locations are assigned as locations of cancer, locations without cancer, and locations with regressed labels between cancer and not cancer. Firstly, a positive that includes the center of the cancer annotation is extracted and defined to be a positive with a highest (e.g., 1.0) certainty level. Then, a set of K patches that include the cancer but not centered are defined as semi-positives. The values that are assigned to these patches depend on the distance from the center of the annotated cancer region, such as normalized in the range of (0, 1). This distance can be Euclidean or follow an exponential drop off. An exponential drop off may avoid an overly wide population of intermediate examples. Locations adjacent to a ground truth location of cancer are assigned regressed labels with a value between cancer and non-cancer. Greater distance from the cancer is assigned a more regressed (i.e., closer to no cancer) label. The cancer negative patches are assigned with a 0 value.

The machine training uses the regression model. The deep-learnt features are used for the regression model or SVM classifier to classify images in an efficient way. By providing the regressed labels, further ground truth information for training is provided. The cancer, no cancer, and regressed labels are used to machine train the classifier. Machine learnt regression followed by thresholding provides classification.

Any machine training may be used. A probabilistic boosting tree, support vector machine (SVM), neural network, sparse auto-encoding classifier, Bayesian network, or other now known or later developed machine learning may be used. Any semi-supervised, supervised, or unsupervised learning may be used. Hierarchal or other approaches may be used.

In one embodiment, the regression model is used to train a regression function. In another embodiment, a multiclass support vector machine is used. K+1 training classes are assigned where K training classes contain positives according to the distance from the center of the cancer and "+1" one set of negative (no cancer). In yet another example, the deep learning is used to train the classifier as well as the feature set.

The classifier is trained to associate the categorical labels (output) to the extracted values of one or more features. The machine-learning of the classifier uses training data with ground truth, such as values for features extracted from frames of data for patients with known outcomes, to learn to classify based on the input feature vector. The resulting machine-learnt classifier is a matrix for inputs, weighting, and combination to output a classification. Using the matrix or matrices, the processor inputs the extracted values for features and outputs the classification. For example, a regression function is used to predict the certainty of a patch to contain cancer.

Additional information may be used for extracting and/or classifying. For example, values of clinical measurements for the patient are used. The classifier is trained to classify based on the extracted values for the features in the frames of data as well as the additional measurements. Genetic data, blood-based diagnostics, family history, sex, weight, and/or other information are input as features for classification.

The classifier is trained to classify the probability that a given patch represents breast cancer. The classifier is trained to classify the tissue into one of two or more classes. The patches of interest are input to the deep-learnt classifier, which outputs values for features. The values are input to the machine-learnt classifier, which outputs the probability of the patch representing cancer. The probability is determined with feature values output by the deep learnt regression or learnt regression function. The determination of probability using the deep learnt network and the regression function as the classifier is one phase of the cascade.

Figure 4:
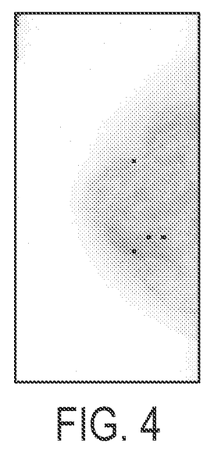
FIG. 4 is an example medical image showing the centers of patches with a probability of breast cancer over a threshold.

FIG. 4 shows an example x-ray image of the breast. The x-ray image includes four dots. The four dots are a probability map output by the classifier of act 18. The intensity of each dot is the probability to represent cancer of the patch associated with the dot. In the example of FIG. 4, the four patches with the highest probability or the probabilities above a threshold are included. Lower probabilities are not included in the probability map.

In act 20, another classifier in the cascade is applied. The classifier refines or recalculates the probability. Alternatively, the classifier finds a specific location within the patch, so classifies locations as cancer or not cancer throughout the patch. A probability map by location for the patch may be output.

Any type of classifier may be used. In one embodiment, a machine-learnt classifier is used. Values for features are extracted from the patch. The features are the same or different as used in other classifiers. For example, a deep learnt network is not used. Instead, feature values obtained by programmed image processing are used. The machine-trained classifier may be trained with a regression model, so that the regression function is used to transform the input features for the patch, with or without the probability from the second phase, into a probability of cancer. In the third phase, patches with high cancer probability are extracted.

The patches with a probability over a threshold from the second phase are classified. The patches output by the second phase that also have a thresholded probability of representing cancer are used to derive the input feature values for the third phase, which then outputs a probability of cancer.

In one embodiment, the classifier operates with kernels of different spatial extent and positions to deal with the arbitrary division of the frame of data to create the patches in the first phase of the cascade. The kernels have any shape and/or spatial extent. For example, rectangles are used. In the third phase, a set rectangles in the environment of the high probability patches are examined and classified as cancer or non-cancer or classified as having a probability of cancer.

The rectangles are shifted spatially by sampling locations in the patch. For example, 10 points are uniformly sampled in the square (e.g., patch) identified with a high probability of cancer in the second phase. Non-uniform and/or other numbers of samples may be used.

One or more kernels are centered over each of the sample locations. A set of kernels is examined in the neighborhood of each high probability patch. Various shapes of rectangles are examined since the cancer shape is typically not fully contained in a square. In one example, for each point, 9 different rectangles with ratios of 1, 1.5, 2, 2.5, and 3 are formed. The rectangles with ratios other than 1 are used twice, with each rotated 90 degrees relative to the other. With the 10 sample points, this results in 90 kernels in total for a patch. Other numbers of kernels, different ratios, or different rotations may be used.

Figure 5:
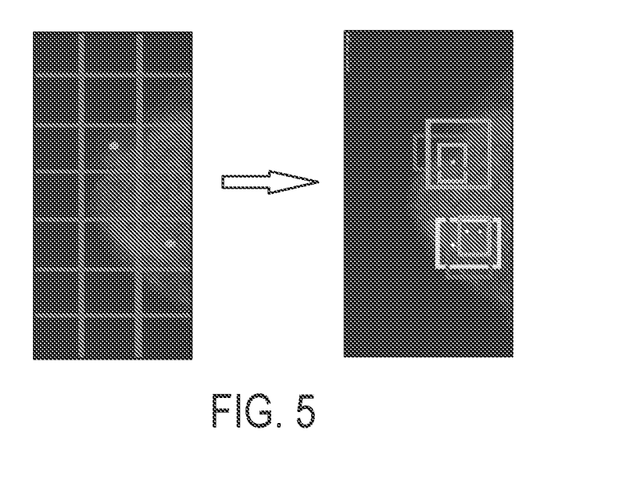
FIG. 5 represents further classification, according to one embodiment, in a cascade for patches with probabilities of cancer above a threshold where the further classification uses multiple different kernels for each patch.

FIG. 5 represents an example. Two patches are identified in the second phase as having a threshold probability of representing cancer. These two patches are marked in the left side of FIG. 5 by dots. The right side shows various rectangles defining the kernels formed around sample points in each of the patches. Some representative rectangles and sample locations rather than all are shown. The kernels define spatial regions that extend out of the patch and/or do not include all the patch. One or more kernels may match the size and shape of the patch.

Each of the kernels is classified. The machine-learnt classifier or other classifier receives features extracted using the kernels as spatial limits and outputs the classification. Classifications are provided for each kernel of each sample point. For extracting features from a patch, smaller kernels may be used. These smaller kernels are positioned throughout the kernel used to define the spatial extent.

The classifications for the patch (e.g., 90 classifications) are combined to determine a classification for the patch. In alternative embodiments, the classifications for each sample point are combined, providing classification by sample point rather than or in addition to classification by patch.

Any combination may be used, such as selecting a maximum probability or averaging the probabilities. Where the classification is binary, a median classification or selection of cancer upon any sample point having a majority of cancer classifications may be used. Other combinations may be used. The combination combines the results of the classification for the kernels. In the Multiclass SVM classifier, the probability is estimated according to the variance of the 10 probabilities, each of the 10 probabilities being based on a combination of the rectangles for the respective sample location. Small variance indicates high probability.

The output classification for a patch or sample point may be a conclusion or result. Alternatively, the output classification is compared to a threshold. The threshold is predetermined, user set, or trained on x-ray images, mammograms, or the current patient. Empirical study may be used to predetermine the threshold level. The threshold is set to avoid or limit false positives and/or false negatives. For example, a patch is classified as containing cancer when the patch has a probability of cancer larger than 0.95. The threshold used depends on the desired false positive rate.

The output may be for sample points, patches, and/or the image. For example, an image with at least one patch with a high probability to contain cancer (e.g., larger than 0.95) is labeled as representing possible cancer. The output is based on the combined results, but may be separate outputs for each kernel, such as in a table with or without combined results. The output may be a set of patches with a probability to contain cancer higher than the predefined threshold. If no patch with high probability is found, the output of the algorithm is that the image is determined to not contain any cancer.

In act 22 of FIG. 1, an indication of breast cancer or not for the patient is displayed. The indication is binary or has a greater number of classes. Any indication may be used, such as an annotation for the image, patch, and/or sample location. A highlight, graphic, or alphanumeric text may be used in a displayed x-ray image. In one embodiment, the indication is by inclusion of the patient and/or image in a set of images to be reviewed. The images identified by the cascade as representing cancer are grouped or displayed separately from other images. Rather than a binary indication, the probability for the image, patch, and/or sample location may be output. The indication may be in a table or patient medical record that links to corresponding x-ray images.

In one embodiment, a physician (e.g., radiologist) causes display of two or more mammography images for a patient. Each image includes an indication for any patches and/or images classified as having breast cancer, such as highlighting or adding a surround graphic for each patch with a probability above the threshold. In another embodiment, each x-ray image with any patch classified as cancer is indicated, but without the patches or sample locations being indicated. The cascade architecture offers the potential to rapidly provide results and assist the physician in review for diagnosis.

Figure 6:
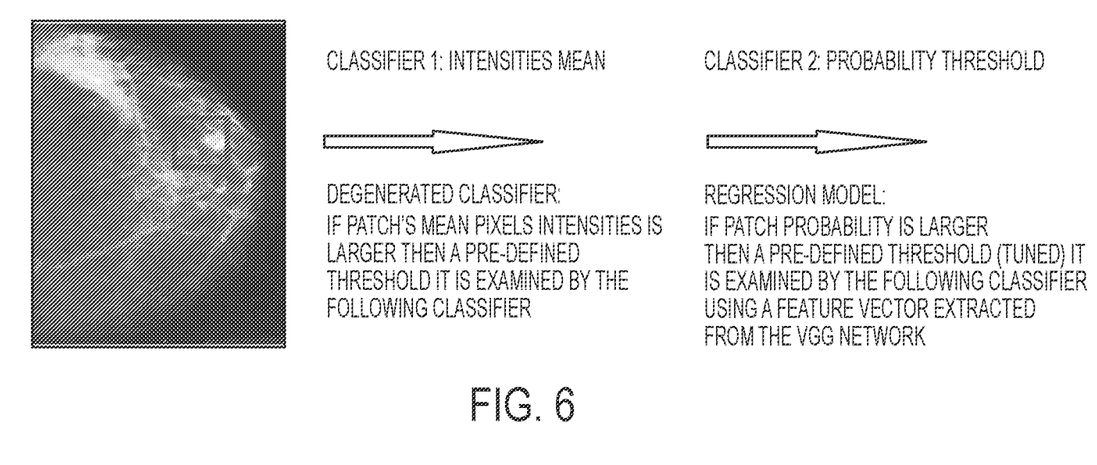
FIG. 6 illustrates an example cascade of two classifiers.

FIG. 6 shows another embodiment of a cascade of classifiers for breast cancer detection in x-ray images. An x-ray image is input to a first classifier, such as the degenerated classifier of act 16. When a mean pixel intensity of a patch is larger than a pre-defined threshold, the patch is passed for further examination by the following classifier. The second and final classifier uses a regression model and deep-learnt network. The deep-learnt network (e.g., VGG) is used to create a feature vector for each of the patches identified as possible cancer from the first classifier. The feature vector is used by a machine-learnt classifier based on a regression function to classify the probability of the patch as representing breast cancer.

In one example, 900 labeled x-ray images are gathered as training data. 250 of the 900 x-ray images include one or more patches that represent cancer. The cascade of FIG. 6 is trained using this training data and regression to create additional samples based on distance from cancer location. When applied, the resulting cascade may achieve a 65% accuracy. Adding further classifiers, more training data, and/or other alterations may improve the accuracy. For example, the VGG layers may be adjusted or tuned using the training data to improve accuracy.

For regression, the training set is collected and labeled according to distance from positives. For example, an exponential distance measure is used. The pre-trained VGG is used to overcome the difficulty of the lack of data and to generate a quality feature vector. Other pre-trained or custom trained networks may be used. The stage is trained as a regression classifier, where each patch is assigned with a value according to the distance from the cancer. In the embodiment including act 20, a zoom-in approach is used. In the three classifier approach of FIG. 1, areas that have a relatively high probability (e.g., above 0.7) to be cancer after the second phase are examined exhaustively with a plurality (e.g., 90) of rectangles or other shapes. 10 or other number of different locations and 9 different ratios between the width and length of the rectangle are used to resample for classification. The entire image, patches, or sample locations are classified according to the maximum probability of all patches or sample locations examined.

The cascade may be trained to output values for staging the tumor. Using advanced tissue characterization provided by an additional machine-learnt classifier, the stage is output. In another embodiment, the classifier is trained to output any information useful for diagnosis or prognosis. For example, information to enhance therapy monitoring is output. An intensity histogram, histogram of difference over time in the intensities representing the tumor, and/or a difference of histograms of intensities representing the tumor at different times are calculated and output without the classifier. The classifier supplements these or other image intensity statistics or histograms. Information derived from the textual features and/or other features is used to provide any information useful to clinicians.

FIG. 7 shows a system for breast cancer detection. The system includes an x-ray scanner 80, a memory 84, a user input 85, a processor 82, and a display 86. Additional, different, or fewer components may be provided. For example, a network or network connection is provided, such as for networking with a medical imaging network, data archival system, or server. In another example, the user input 85 is not provided. In other examples, a server connects through a network with many x-ray scanners 80 and/or processors 82 to provide or assist in application of a cascade to x-ray images.

The processor 82, memory 84, user input 85, and/or display 86 are part of the medical x-ray scanner 80. Alternatively, the processor 82, memory 84, user input 85, and/or display 86 are part of an archival and/or image processing system, such as associated with a medical records database workstation or server, separate from the x-ray scanner 80. In other embodiments, the processor 82, memory 84, user input 85, and/or display 86 are a personal computer, such as desktop or laptop, a workstation, a server, a network, or combinations thereof. The processor 82, display 86, user input 85, and/or memory 84 may be provided without other components for acquiring data by scanning a patient.

The x-ray scanner 80 is a computed tomography (CT), x-ray, fluoroscopy, or mammography imager. In one embodiment, the x-ray scanner 80 is a mammography imaging system including positioning devices for a breast, an x-ray source, and an x-ray detector. The x-ray source and detector scan or image the positioned breast tissue of a patient.

The memory 84 may be a graphics processing memory, a video random access memory, a random access memory, system memory, cache memory, hard drive, optical media, magnetic media, flash drive, buffer, database, combinations thereof, or other now known or later developed memory device for storing data. The memory 84 is part of the x-ray scanner 80, part of a computer associated with the processor 82, part of a database, part of another system, a picture archival memory, or a standalone device.

The memory 84 stores one or more frames of data or x-ray images representing a breast of the patient. Segmentation or tissue region information (e.g., patch or kernel), features, feature values, classification results, a machine-learnt matrix, classifiers, and/or images are stored. The memory 84 may alternatively or additionally store data during processing, such as storing classification outputs, probabilities, thresholds, or other information discussed herein.

The memory 84 or other memory is alternatively or additionally a non-transitory computer readable storage medium storing data representing instructions executable by the programmed processor 82 for breast cancer detection. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The user input 85 is a keyboard, mouse, trackball, touch pad, buttons, sliders, combinations thereof, or another input device. The user input 85 may be a touch screen of the display 86. User interaction is received by the user input, such as a designation of a region of tissue (e.g., a click or click and drag to place a region of interest), threshold setting, or image review. Other user interaction may be received, such as for activating the classification, segmenting breast tissue, and/or review of classification results.

The processor 82 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for segmentation, extracting feature values, and/or classifying. The processor 82 is a single device or multiple devices operating in serial, parallel, or separately. The processor 82 may be a main processor of a computer, such as a laptop or desktop computer, or may be a processor for handling some tasks in a larger system, such as in an x-ray scanner 80. The processor 82 is configured by instructions, design, hardware, firmware, and/or software to perform the acts discussed herein.

The processor 82 is configured to apply a cascade of classifiers. One or more of the classifiers includes a deep-learnt network initially trained from image data that is not mammography data, not x-ray data, and/or not medical imaging data. Alternatively or additionally, one or more of the classifiers uses a regression function.

The display 86 is a monitor, LCD, projector, plasma display, CRT, printer, or other now known or later developed devise for outputting visual information. The display 86 receives images, graphics, text, quantities, or other information from the processor 82, memory 84, x-ray scanner 80, or server 88. One or more medical images are displayed. The images are of a region of the patient. In one embodiment, the images are of breast tissue, such as mammograms with any images, patches, and/or sample locations classified as cancerous highlighted by opacity or color. The image includes an indication, such as a text, a graphic or colorization, of the classification. Alternatively or additionally, the image includes a quantity based on the classification, such as the probability. The quantity or classification output may be displayed as the image without the medical image representation of the patient. Alternatively or additionally, a report with the classification is output.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for breast cancer detection with an x-ray scanner, scanner, the method comprising:

scanning a patient with the x-ray scanner, the scanning providing a frame of data representing breast tissue in the patient;

classifying patches of the frame of data as of interest or not based on intensity;

determining a probability of breast cancer for the patches that are of interest using a deep learnt regression at least partially trained on non-x-ray data, the probability not determined for the patches not of interest, the determining comprising inputting the patches that are of interest into the deep learnt regression, the deep regression outputting feature values;

classifying the patches with the probability over a threshold using a machine-learnt classifier and not classifying the patches with the probability below the threshold; and displaying an indication of breast cancer for the patient based on an output of the classifying using the machine-learnt classifier.

2. The method of claim 1 wherein scanning comprises acquiring a mammogram.

3. The method of claim 1 wherein classifying the patches based on intensity comprises dividing the frame of data into the patches, calculating mean intensity for each of the patches, and classifying based on the mean intensity.

4. The method of claim 1 wherein determining the probability comprises using the regression model based on intermediate features assigned to first locations adjacent to second locations with higher probabilities and to third locations with lower probabilities.

5. The method of claim 1 wherein classifying using the machine-learnt classifier comprises classifying with the machine-learnt classifier learned with regression.

6. The method of claim 1 wherein classifying using the machine-learnt classifier comprises sampling locations in each patch, classifying with the machine-learnt classifier for kernels centered at the sampling locations, combining results of the classifying for the kernels, and providing the output as a function of the combined results.

7. The method of claim 1 wherein displaying comprises displaying an image from the frame of data with highlighting of locations for the patches classified using the machine-learnt classifier as having breast cancer.

8. The method of claim 1 wherein displaying comprises displaying an x-ray image from the frame of data when any of the patches classified using the machine-learnt classifier is classified as having breast cancer.

9. A method for machine training a classifier for breast cancer detection, the method comprising:

acquiring a set of x-ray images with ground truth labels for first locations of breast cancer;

assigning adjacent locations to the first locations with regressed labels of breast cancer and second locations spaced from the first locations as ground truth labels of no breast cancer, the regressed labels being based on a distance transform and reduction from the ground truth labels; and machine training a cascade of classifiers, at least one of the cascade of classifiers trained using the ground truth labels of breast cancer for the first locations, the regressed labels for the adjacent locations, and the ground truth labels of no breast cancer for the second locations.

10. The method of claim 9 wherein assigning comprises assigning the regressed labels as a function of distance from the ground truth labels of breast cancer for the first locations, greater distance having greater regression.

11. The method of claim 9 wherein the machine training comprises training the cascade of the classifiers as first and second classifiers, the first classifier trained using the ground truth labels of breast cancer and no breast cancer, the second classifier trained using the regressed labels.

12. The method of claim 9 wherein machine training comprises machine training with feature values output by a deep learnt network trained on image data other than medical imaging data.

13. The method of claim 12 wherein machine training with the deep learnt network comprises machine training with the deep learnt network trained with the x-ray images.

14. The method of claim 12 wherein machine training comprises machine training with a regression analysis.

15. The method of claim 12 wherein machine training comprises machine training with a support vector machine operable with the regressed labels.

16. A method for breast cancer detection with an x-ray scanner, the method comprising:

scanning a patient with the x-ray scanner, the scanning providing a frame of data representing breast tissue in the patient;

determining a probability of breast cancer for the patient with a deep learnt network initially trained on image data for objects other than breast tissue, the probability determined with feature values output by the deep learnt network and with a learnt regression function;

displaying an indication of breast cancer for the patient based on the probability.

17. The method of claim 16 wherein determining the probability is a first classifier phase of a cascade of classifier phases.

18. The method of claim 16 wherein determining the probability comprises determining with the deep learnt network trained on image data from optical photographs of the objects in a non-medical environment, and with the deep learnt network incrementally trained with x-ray images.

* * * * *